US009675310B2

(12) United States Patent
Kelm et al.

(10) Patent No.: US 9,675,310 B2
(45) Date of Patent: Jun. 13, 2017

(54) REGRESSION FOR PERIODIC PHASE-DEPENDENT MODELING IN ANGIOGRAPHY

(71) Applicants: Michael Kelm, Erlangen (DE); Peng Wang, Princeton, NJ (US); Andreas Meyer, Bubenreuth (DE); Guillaume Dumont, Plainsboro, NJ (US)

(72) Inventors: Michael Kelm, Erlangen (DE); Peng Wang, Princeton, NJ (US); Andreas Meyer, Bubenreuth (DE); Guillaume Dumont, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 80 days.

(21) Appl. No.: 14/266,191

(22) Filed: Apr. 30, 2014

(65) Prior Publication Data
US 2015/0313563 A1 Nov. 5, 2015

(51) Int. Cl.
  *A61B 6/00* (2006.01)
  *A61B 6/12* (2006.01)
  *A61M 25/09* (2006.01)
  *G06T 7/277* (2017.01)

(52) U.S. Cl.
  CPC .............. *A61B 6/481* (2013.01); *A61B 6/12* (2013.01); *A61M 25/09* (2013.01); *G06T 7/277* (2017.01); *G06T 2207/10016* (2013.01); *G06T 2207/10121* (2013.01); *G06T 2207/30021* (2013.01); *G06T 2207/30101* (2013.01)

(58) Field of Classification Search
  CPC . A61B 6/12; A61B 6/504; A61B 2017/00252; A61B 2017/00694; A61B 2017/00703
  See application file for complete search history.

(56) References Cited

U.S. PATENT DOCUMENTS

| 5,274,551 | A  | * | 12/1993 | Corby, Jr. | ............. | A61B 6/463 348/45 |
| 2003/0161526 | A1 | * | 8/2003 | Jupiter | ................ | G01N 23/046 382/154 |
| 2008/0247621 | A1 | * | 10/2008 | Zarkh | ...................... | A61B 6/12 382/130 |
| 2008/0275335 | A1 | | 11/2008 | Zhang et al. | | |
| 2010/0312100 | A1 | * | 12/2010 | Zarkh | ...................... | A61B 6/12 600/424 |
| 2011/0112398 | A1 | | 5/2011 | Zarkh et al. | | |
| 2011/0319752 | A1 | * | 12/2011 | Steinberg | ................ | A61B 6/12 600/424 |
| 2012/0004529 | A1 | * | 1/2012 | Tolkowsky | .......... | A61B 6/5217 600/407 |
| 2012/0004533 | A1 | | 1/2012 | Peng et al. | | |

(Continued)

OTHER PUBLICATIONS

P. Wang, et al., "Robust Guidewire Tracking in Fluoroscopy," Computer Vision and Pattern Recognition, IEEE Conference, pp. 691-698, Jun. 2009.

*Primary Examiner* — Baisakhi Roy

(57) ABSTRACT

A periodic time-varying model of a guide wire, other device, or vessel is created from higher contrast CINE acquisition. A multivariate curve regression is used for periodic, phase dependent motion modeling. This model is then used to locate or track the guide wire, other device or vessel in lower contrast fluoroscopy images during intervention.

20 Claims, 3 Drawing Sheets

(56) References Cited

U.S. PATENT DOCUMENTS

| | | | |
|---|---|---|---|
| 2012/0004537 A1* | 1/2012 | Tolkowsky | A61B 8/12 600/424 |
| 2012/0029339 A1* | 2/2012 | Cohen | A61B 6/12 600/407 |
| 2012/0207359 A1* | 8/2012 | Konukoglu | G06T 7/0034 382/128 |
| 2013/0011041 A1 | 1/2013 | Florent et al. | |
| 2013/0230136 A1* | 9/2013 | Sakaguchi | H04N 13/00 378/41 |
| 2015/0065848 A1* | 3/2015 | Choi | G06F 19/3437 600/407 |

* cited by examiner

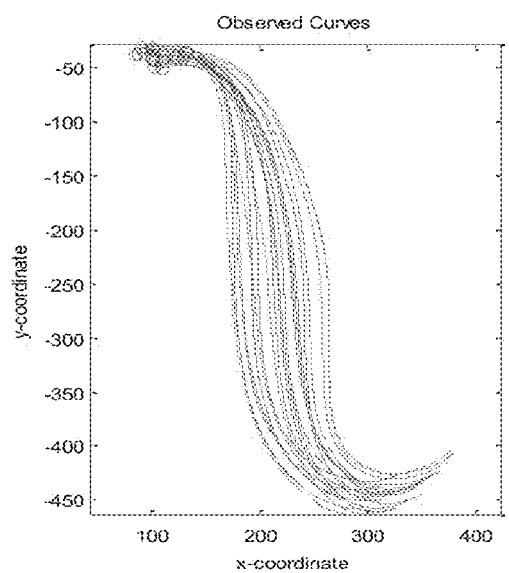 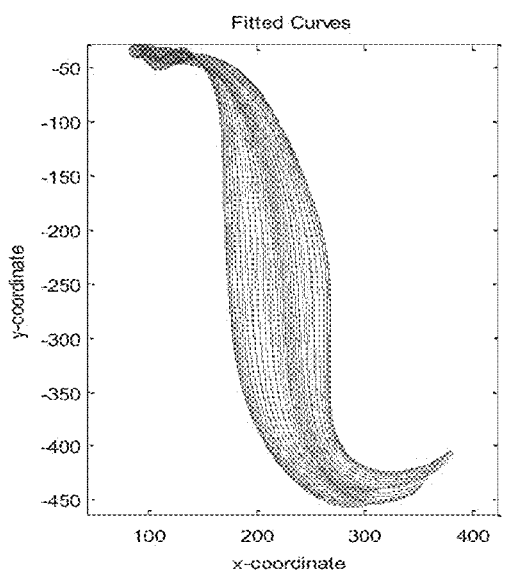
FIG. 5A    FIG. 5B
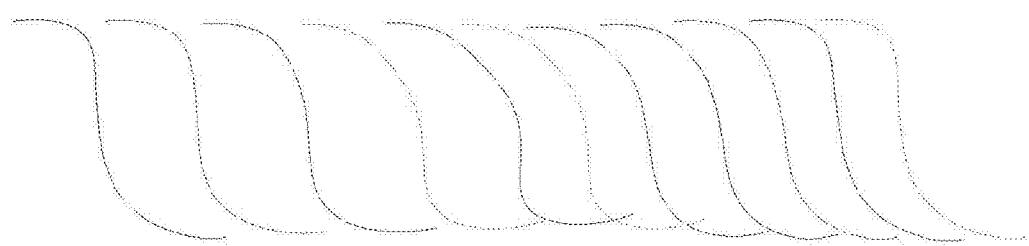
FIG. 6

REGRESSION FOR PERIODIC PHASE-DEPENDENT MODELING IN ANGIOGRAPHY

BACKGROUND

The present embodiments relate to identifying a location of a medical device or structure in an image, such as locating a guide wire or vessel for treating coronary artery disease. Coronary artery disease (e.g., occurrence of coronary stenosis) is among the most frequent diseases. Current standard diagnosis and interventional treatment is coronary angiography and angioplasty under fluoroscopy.

During the intervention for coronary artery disease, different acquisition modes are employed. High-quality images (e.g., CINE Acquisition) are acquired to resolve details and localize the target stenosis after injection of a contrast medium. During navigation phases, when the interventional cardiologist tries to advance a guide wire to the position of the occlusion, an acquisition mode of imaging with less dose and thus reduced image contrast is employed (e.g., fluoroscopy). Fluoroscopy is used for real-time monitoring of the procedure and catheter location visualization. Metal guide wires may be viewed in fluoroscopic images, but unreliably. Vessels are more difficult to view, especially since injected contrast agent is not typically provided for fluoroscopy. 2D fluoroscopic images lack detailed anatomical information due to the incapability of X-ray in distinguishing among soft tissues and low dosage. For example, interventional treatment of Chronic Total Occlusion (CTO) of the coronary arteries is a complicated and time consuming process due to the lack of visibility of the occluded vessels under fluoroscopy.

It is desirable to provide visual guidance for the recanalization of the occluded vessel segment. This is particularly true for the antegrade approach, where no retrograde wire is used that could indicate the direction for the antegrade wire. Locating the vessel or guide wire without the use of prior information may be difficult. In interventions, the guiding catheter tip, vessel, and guide wire are undergoing motions, such as due to breathing or the heart cycle. Using Kalman filtering as a motion prior may assist in locating the guide wire and/or vessel.

BRIEF SUMMARY

By way of introduction, the preferred embodiments described below include methods, systems, instructions, and computer readable media for modeling in angiography. A periodic time-varying model of the guide wire, other device, or vessel is created from higher contrast CINE acquisition. A multivariate curve regression is used for periodic, phase dependent motion modeling. This model is then used to locate or track the guide wire, other device, or vessel in fluoroscopy images during intervention.

In a first aspect, a method is provided for modeling in angiography. A first sequence of frames of CINE acquisition data is obtained. The CINE acquisition data of the frames represents a curved medical device over a physiological cycle. The curved medical device is modeled as a function of phase of the physiological cycle. The modeling provides a time-varying model of the curved medical device. A second sequence of frames of fluoroscopy data is obtained. The fluoroscopy data of the frames represents the curved medical device over the physiological cycle. The curved medical device is tracked in the frames of the fluoroscopy data as a function of the time-varying model of the curved medical device. A fluoroscopy image of the curved medical device is generated. The fluoroscopy image indicates the curved medical device from the tracking.

In a second aspect, a non-transitory computer readable storage medium has stored therein data representing instructions executable by a programmed processor for modeling in angiography. The storage medium includes instructions for creating a periodic time-varying model of a curved medical device from first images of a patient, predicting a shape of the curved medical device in second images of the patient with the periodic time-varying model, the predicting being a function of phase of a cycle, and displaying a sequence of the second images with the curved medical device enhanced using the predicted shape.

In a third aspect, a system is provided for modeling in angiography. A memory is operable to store data representing, at different times, a region of a patient and a guide wire in the patient. A processor is configured to estimate position, for each of different phases, of the guide wire from the data. The position is estimated as a function of a regressor with sine, cosine, or sine and cosine features. The processor is configured to locate the guide wire in fluoroscopy images as a function of the positions at the different phases. A display is operable to display the fluoroscopy images of the different phases with the located guide wire.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 4A and 5A show observed curves over a heart cycle of a guide wire in two examples, respectively, and FIGS. 4B and 5B show regression fitted curves over the heart cycle of the examples of FIGS. 4A and 5A, respectively; and FIG. 6 shows the fitted curves of FIG. 5B spaced apart to show the periodicity.

DETAILED DESCRIPTION OF THE DRAWINGS AND PRESENTLY PREFERRED EMBODIMENTS

Accurate detection of a medical device or vessel in a medical image may be difficult. Locating the guide wire or vessel in fluoroscopy images is a challenging task since most structures in the displayed images are constantly moving due to cardiac motion and breathing motion. Since the coronary vessels are attached to the surface of the heart, their shape changes periodically with the cardiac phase. The cardiac phase may be inferred from the electrocardiogram (ECG), which is available and synchronized with the acquired sequences. Minor influence may also come from breathing motion. The breathing phase may be inferred from a breathing sensor or from the image data itself.

A time-varying model is created for the guide wire and/or the targeted occluded vessel using CINE acquisitions with injected contrast. The phase information (e.g., cardiac and/or breathing motion) is exploited for a direct estimate of curve shape in the model. Periodic behavior is enforced by a feature transform in a multivariate curve regression. A low number of training examples (e.g., 10-30) is tolerable because of regularized linear regression and a curve smoothness prior. This model is then used to track the guide wire and/or for estimating the location of the target vessel during navigation with fluoroscopy.

There may be different applications. In the example discussed below and shown in the Figures, interventional angiography using a guide wire is provided. The location of the guide wire and/or vessel in the angiography data is identified. These locations may be used to generate a model for then tracking the guide wire and/or vessel in fluoroscopy images. Other applications include any catheter, stent, or other procedure where the location of a medical device or vessel in medical imaging is to be automatically identified by a computer. For example, a catheter, a needle, or a pigtail catheter are tracked in image guided interventions.

Figure 2:
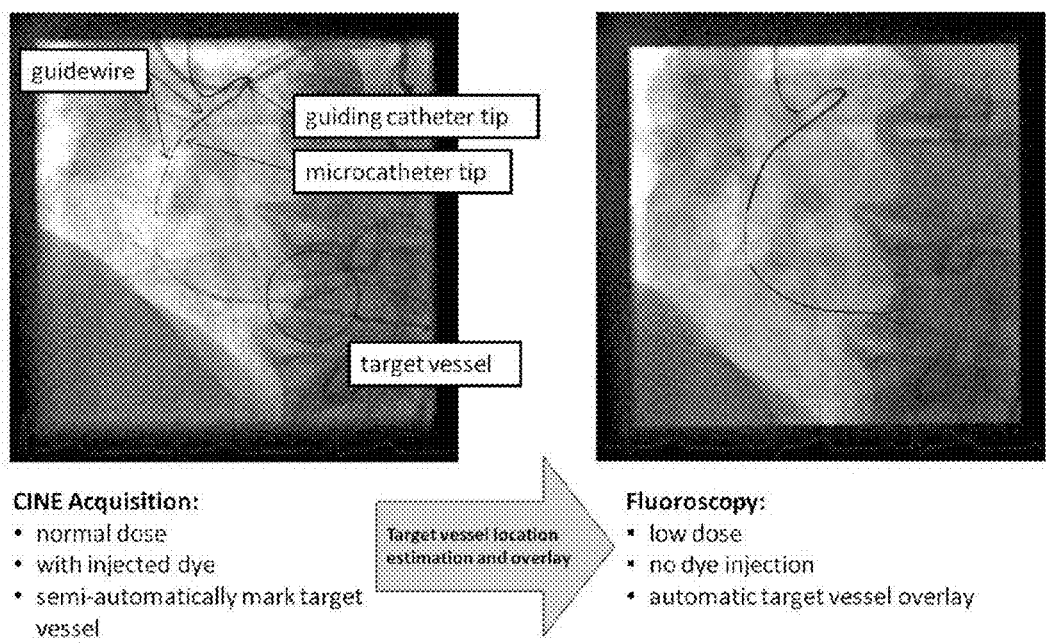
FIG. 2 illustrates one embodiment of a method for modeling in angiography.

FIG. 2 shows a method for modeling in angiography. In general, CINE acquisition is used to acquire two-dimensional x-ray images of the patient. The images for CINE acquisition have a greater x-ray dose than fluoroscopy, since a fewer number of such images may be acquired. Injected dye is used to increase contrast, allowing greater visibility of vessels than without the injected contrast agents (e.g., see image on the left of FIG. 2). The guide wire, guiding catheter, micro catheter, target vessel, and/or other structure may be identified or located and modeled in each of the images. This modeling occurs prior to intervention. A time-varying model for the guide wire and/or the target vessel that is based on cardiac and/or breathing phase is generated. The models for the guide wire and/or the target vessel are extracted from the high contrast CINE acquisition.

During intervention, one or more fluoroscopy images (e.g., see image on the right of FIG. 2) are acquired. The fluoroscopy images have a lower x-ray dose and no or little dye injection. The modeling is used to determine the most likely location of the guide wire and/or vessel in the fluoroscopy image. Rather than detecting the structure from the image using the same detection, the modeled curve is registered with the image, providing a best match. The time-varying model is used to automatically detect and track the guide wire in lower-dose and contrast fluoroscopy. The guide wire position may be used to estimate the target vessel location.

Figure 3:
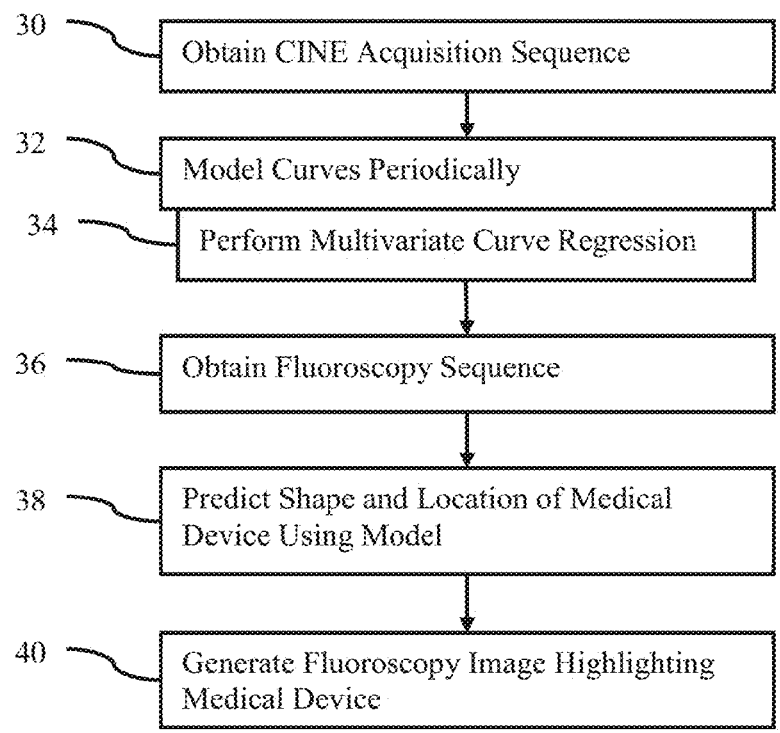
FIG. 3 is a flow chart diagram of one embodiment of a method for modeling in angiography.

FIG. 3 shows a flow chart diagram of a method for modeling in angiography. An example embodiment for implementing the method of FIG. 2 is provided. Images with greater contrast are used to model structure relying on periodic motion, such as using a multivariate curve regression. The model is used to locate the structure in images with lower contrast during intervention.

Figure 1:
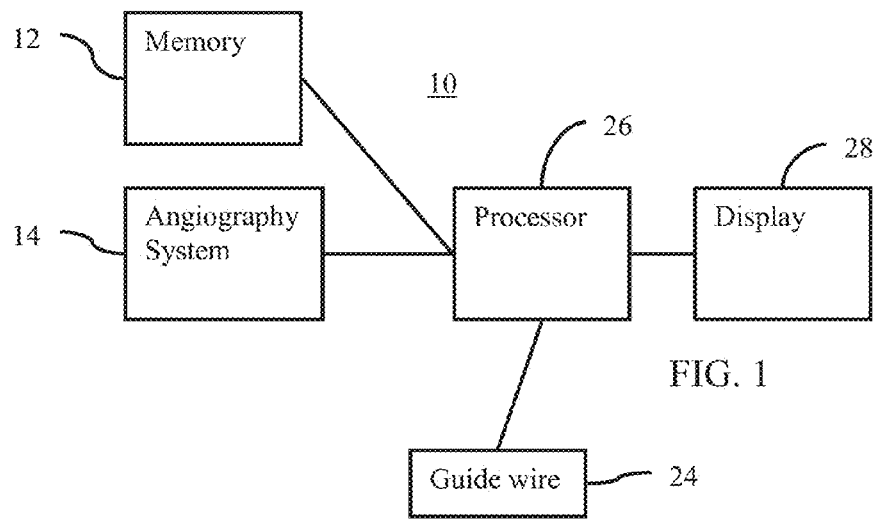
FIG. 1 is a block diagram of one embodiment of a system for modeling in angiography.

The method is implemented by the system 10 of FIG. 1, a computer, an x-ray system, a processor, or another system. For example, a processor performs acts 32, 34, 38, and 40. The processor controls an x-ray system (e.g., angiography or fluoroscopy system) or obtains from an x-ray system the sequences of data in acts 30 and 36.

The acts are performed in the order shown or other orders. For example, the fluoroscopy sequence is obtained in act 36 while the modeling of acts 32 and 34 are performed. Acts 36, 38, and 40 may be performed in an ongoing manner, such as generating an image in act 40 while another frame of data of the sequence is obtained in act 36. As or immediately after (e.g., 2 seconds or less) each frame is obtained in act 36, the location of the structure is found in a previous frame in act 38.

Additional, different, or fewer acts may be provided. For example, the output act 40 is not provided, but instead the locations are used for automated guidance or stored. As another example, acts for injection of contrast dye, performing the intervention, and/or other uses of the predicted location are performed.

In act 30, a sequence of frames of data is obtained. The frames of data are obtained from an x-ray system, such as by scanning a patient. Any angiography scanning may be used. Alternatively, the frames of data are obtained by loading from memory or receiving a transmission of the data.

The sequence of frames represents the patient or part of the patient over a period. Any period may be used, such as frames over 2-3 seconds. Any frame rate may be provided, such as 5-20 frames per second.

The frames of the sequence are acquired at times or phases of a physiological cycle. For example, ECG measurements are made while acquiring the frames. Each frame is synchronized or labeled with a phase of the heart cycle as measured with the ECG device. Different frames of a given heart cycle represent the patient at different phases. More than one frame may represent the patient at a same phase, such as for frames acquired during different cycles. The acquisition of the frames may be triggered so that frames representing the same or specific phases of the different cycles are obtained.

The frames obtained are CINE acquisition images. The images are frames of data displayed as an image or to be processed to be displayed as an image. For example, the frames of data are detected intensities with or without mapping to gray scale, filtering, or other image processing.

For CINE acquisition in angiography imaging, a contrast agent (e.g., iodine or other dye) may be injected into the patient. The contrast agent provides a detectable response to x-rays. By flowing through the circulatory system, the contrast agent may provide detectable response highlighting the circulatory system, such as the vessels, veins, and/or heart. By transmitting x-rays through the patient to the detector, a projection image is provided. The frame of data represents detection along two-dimensions. Any tissue, bone, guide wire, and contrast agent along the path of travel of the x-ray beam interacts with the x-rays, causing a detectable difference in intensity at the detector. Since each pixel or location of the detector represents an accumulation of responses along the path of travel, the CINE acquisition images are a projection image of the region of the patient.

The CINE acquisition data represents curved structure in the patient. The projection of the guide wire, vessel, and/or other medical device provides a curved structure. By obtaining frames over multiple phases and/or heart cycles, a series of curves of the structure are represented in the sequence. The series of curves are a curved structure or one curve changing over time. Due to heart and/or breathing motion, the curve changes periodically and regularly over each cycle.

The structure is identified in each of the frames of the CINE acquisition data. The identification uses any approach, such as manual, automatic, or semi-automatic. For example, the user indicates a guide wire and/or vessel with a stenosis. Based on the user indication of a point, line, or area, a processor performs analysis to extract other locations for the vessel and/or guide wire. Thresholding, filtering, or other approaches may be used.

Automated or computer assisted detection may identify one location for the structure or may identify multiple possible locations for the structure and select one of the possible locations at the location. Any now known or later developed detection may be used to provide the candidate locations. In one example, learning-based detectors are used for object detection. The learning-based classifier is trained from a set of off-line collected data, including both object samples (positive) and non-object samples (negative), to learn the decision boundary that separates the positive from negative samples. Learning based detection adapts for different detection tasks, such as learning to detect different types of devices. One example learning-based classifier is the probabilistic boosting tree (PBT). PBT is a tree-based generalization of AdaBoost classifiers for modeling a complex distribution of a class of objects. The classifiers are trained from any one or more types of features, such as using Haar features. The detectors may be constructed in a hierarchical way. First, a position detector is trained to locate the position of objects. An orientation detector is then trained at images rotated at different angles to detect devices at arbitrary orientations. Furthermore, a size detector is applied to search across different scales by varying the size of Haar features. Each detection candidate for each medical device or other structure is associated with a confidence score that is provided by the PBT. Other approaches may be used.

The same or different detector is applied for different structures (e.g., different medical devices) where there are multiple structures being detected.

The detection is performed for each image or frame in the sequence. Alternatively, detection is performed for an initial frame and tracking is used to find the location in other frames. For example, the location of the guide wire is detected. The guide wire may be indicated by the user (e.g., tracing) in one frame and tracked to determine the location in other frames. Alternatively, the guide wire is detected by filtering to enhance linear, curve, or line structures. Gradient-based, pattern matching, region growing or other detection is used to determine the location of the guide wire in each frame.

Alternatively or additionally, the motion of the guide wire is determined. The change in the position in the guide wire is determined. The guide wire is treated as having a constant curve, so one motion vector of translation and rotation of the guide wire may be employed as input data. In other embodiments, the motion includes one or more factors for change in curve or bend.

Figure 4A:
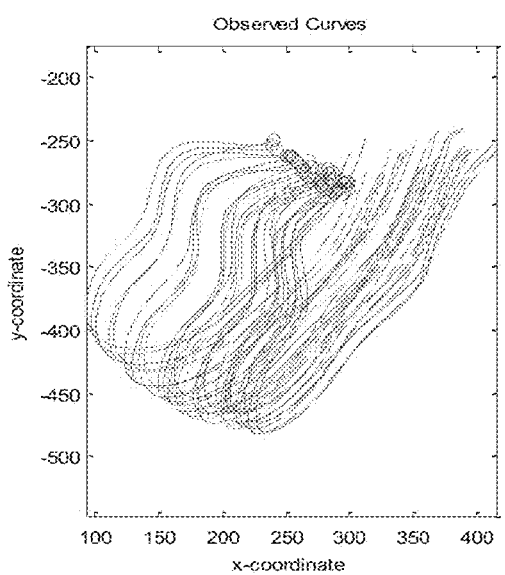

FIGS. 4A and 5A show examples of curves observed throughout a heart cycle. Each observed curve is the detected location of the guide wire at a given phase. The observed curves correspond to the guide wire detected in CINE acquisition images. A curve is observed or detected for each image during the heart cycle. Multiple images for a same phase may be used. FIGS. 4A and 5A show the respective observed curves of one heart cycle.

Referring again to FIG. 3, the observed curves (e.g., detected guide wire) from the CINE acquisition are modeled in act 32. The phase information of the physiological cycle is used for modeling the set of observed curves as a periodic time-varying model. For example, the curves of the detected guide wire of FIGS. 4A and 5A are used to create or construct the fitted curves of FIGS. 4B and 5B. The time-varying model is the set of curves by phase of the cycle fitted to the detected curves. The fitting may remove noise and provide for constraints on the estimated locations of the medical device over time as compared to the observed curves.

The model is constructed from the images of the patient. The observed curves or detected structure from the images is used to create the model. The model is of a set of curves over various phases of a cycle. Each fit curve for each phase is a model for that phase. The collection of models over two or more phases provides a time-varying model. The collection of models over a cycle provides a periodic time-varying model. Due to cyclic motion, the periodic time-varying model represents the structure in any given cycle.

To construct the periodic, time-varying model, a curve of the structure (e.g., guide wire) is estimated for each of a plurality (e.g., 2-20 phases) of different phases of the physiological cycle. The observed curves are provided as a set of N curves $y_n$ (n=1 . . . N), each represented by a polygon with K D-dimensional points $y_{nk} \in \Re^D$ (k=1 . . . K), thus $y_n \in \Re^{DK}$. For each curve, associated phase information $\tau_n$ is available as well from ECG or other source (e.g., sensor and/or estimate from image data). Since x-ray projection imaging is used in the CINE acquisition, the curves are represented by points along two dimensions, i.e. $y_{nk} \in \Re^2$. Points in three-dimensions could be used, such as for computed tomography (CT), magnetic resonance (MR) or ultrasound data. Also, while the examples below only use cardiac phase, i.e., $\tau_n \in [0,1]$, additional periodic cycles may be included. For example, vector-valued phases ($\tau_n \in [0,1]^R$) including both cardiac and breathing phases together are accounted for in modeling.

To estimate the curves of the time-varying model from the observed curves, a multivariate curve regression is performed. The curved medical device or other structure that undergoes periodic motion is modeled using the detection of the device or structure from the CINE acquisition. The modeling estimates a regressor with minimization of an energy function including parameters of the regressor. From the N observed curves, a function $y(\tau):[0,1]^R \to \Re^{DK}$ is computed. The function provides an estimate of the curve c for a certain phase, characterized by the phase vector $\tau$. Thus, the model construction problem is cast as a regression problem.

Since the model is periodic, the periodic behavior of the time-varying model is enforced. In order to enforce periodic behavior of the regressed function $y(\tau)$ with respect to $\tau \in [0,1]^R$, a periodic feature function $f^W(\tau)$ with a certain maximum frequency $W \cdot 2\pi$ is defined. The feature function is made periodic with cosine, sine, or cosine and sine terms. Only periodic or at least one or more periodic terms are included in the feature vector to be regressed. For example, both sine and cosine features are used in the regression. Every point of each fitted curve is a linear combination of sine and cosine components. For one-dimensional phase information (R=1—only cardiac phase), an example feature function may be:

$$f_1^W(\tau)=[\cos(\omega_1\tau), \sin(\omega_1\tau), \cos(\omega_2\tau), \sin(\omega_2\tau), \ldots, \cos(\omega_W\tau), \sin(\omega_W\tau)]$$

where $\omega_k=k \cdot 2\pi$. For R>1 (i.e., more than one cyclic, such as both breathing and heart), the feature function is constructed by including analogous sine and/or cosine features for each of the R phase dimensions independently with potentially different maximum frequencies $W_r \cdot 2\pi$:

$$f(\tau)=f_R^W(\tau)=[f_1^{W_1}(\tau_1), f_2^{W_2}(\tau_2), \ldots, f_R^{W_R}(\tau_R)],$$

where $$W = \sum_{r=1}^{R} W_r$$

and thus $f(\tau) \in \mathfrak{R}^{2W}$. For example, for R=2, an example function is:

$$f_2^W(\tau) = [\cos(\omega_1 \tau_1), \sin(\omega_1 \tau_1), \ldots, \cos(\omega_{W_1} \tau_1), \sin(\omega_{W_1} \tau_1), \cos(\omega_1 \tau_2), \sin(\omega_1 \tau_2), \ldots, \cos(\omega_{W_2} \tau_2), \sin(\omega_{W_2} \tau_2)]$$

Other functions with periodic terms, with or without sine and/or cosine, may be used.

To create the model, a regression function $Y_\beta(f^W(\tau)) = \hat{y}(\tau)$ where $\beta$ are the parameters of the regressor is estimated. A non-linear regressor, such as a Random Forest, may be used. In one embodiment, a regularized linear regression is used. Other regressor functions may be used. With the regularized linear regression, the regressor is estimated from the training sample $\{\tau_n, y_n\}_{n=1}^N$ (observed curves for a given patient) in a least squares sense. This estimation effectively assumes noise to be Gaussian. Other noise functions may be incorporated. The estimation minimizes an energy function with respect to the parameters, $\beta$. The minimization may be represented as:

$$\hat{\beta} = \underset{\beta}{\operatorname{argmin}} \left( \sum_{n=1}^{N} \|y_n - \beta^T [1; f(\tau_n)]\|^2 + \|\Gamma \beta \Delta^T\|^2 \right) = \underset{\beta}{\operatorname{argmin}} (\|Y - X\beta\|^2 + \|\Gamma \beta \Delta^T\|^2), \quad (3)$$

with the sought coefficients $\beta \in \mathfrak{R}^{F \times DK}$, where $Y \in \mathfrak{R}^{N \times DK}$ is a matrix, which stacks all N example curves from the training set, and where $X \in \mathfrak{R}^{N \times F}$ (F=2W+1) is a matrix, which has a constant term (i.e., non-periodic spatial offset) in the first column and holds the features $f(\tau_n)$ for each training example in the remaining columns (i.e., periodic components).

The estimation of the model may be constrained. For example, smoothness and/or shrinkage within a curve and/or between curves are constrained. Constraining may limit the model based on physical properties of the structure. For example, the guide wire is unlikely to stretch or contract, so shrinkage is limited. As another example and depending on the view direction and location in the patient, the amount of curvature of the guide wire may be limited (i.e., no buckling). Given the projection nature of x-ray imaging, some more extreme appearances of curvature may occur.

In one embodiment, the estimating is constrained between points of a curve of the curved medical device, and/or differences between features of the energy function are constrained. While the regularizer $\Gamma \in \mathfrak{R}^{F \times F}$ may be used to describe coefficient constraints on or between features (e.g. shrinkage), $\Delta \in \mathfrak{R}^{DK \times DK}$ may be used to describe coefficient constraints on or between curve points (e.g. smoothness constraints such as first or second order differences). Neighboring points on a curve are constrained to move in similar directions and magnitudes. Since the coefficients or parameters of the regressor may not be stable, the constraints may regularize the coefficients or parameters of the regressor for neighboring points on the curves.

The minimization function may be solved analytically by employing the vectorized operator (vec), which stacks a matrix column by column and the Kronecker product $\otimes$ as $$vec(\hat{\beta}) = \underset{\beta}{\operatorname{argmin}}(\|vec(Y) - (I_{DK} \otimes X)vec(\beta)\|^2 + \|(\Delta \otimes \Gamma)vec(\beta)\|^2)$$

$$= (I_{DK} \otimes X^T X + \Delta^T \Delta \otimes \Gamma^T \Gamma)^{-1}(I_{DK} \otimes X^T)vec(Y)$$

Although the dimensions of the matrices may be large, the matrices are sparse and may efficiently be solved by any sparse linear solver. Where the identity matrix is equal to the spatial constraint (e.g., $\Delta = I_{DK}$—no curve smoothness prior), the vec decouples and may be solved point-to-point or more efficiently than with a sparse linear solver.

Figure 4B:
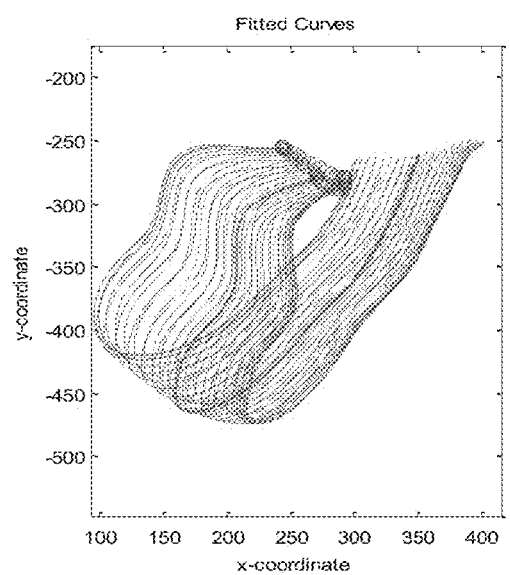

In the examples of FIGS. 4B and 5B, curves constructed as periodic-time varying models are shown. Using the observed curves of FIGS. 4A and 5A, the model fitted curves created using the vec function above in FIGS. 4B and 5B, respectively, are provided. The model provides guide wire curves obtained from the fitted regression model. Only cardiac phase (R=1) is used for these examples. The curves represent the guide wire over a cycle. For a given phase of any cycle, one of the curves is provided. The same curve represents the guide wire for a given phase of any cycle.

FIG. 6 shows the fitted curves of the periodic, time-varying model spaced apart. Curves are estimated at equidistant phases, but estimation at specific phases that are not equidistant may be used. In FIG. 6, the curves are plotted spread apart, side-by-side to show the periodicity. The beginning and ending curves represent similar or the same phase, so are similar or same shape (e.g., the shape at phase 0.0 and phase 1.0 (same phase) are equal). The varying curve shapes are periodical.

Referring again to FIG. 3, the periodic, time-varying model, represented by the phase aligned fitted curves, is used to locate the same structure in one or more fluoroscopy images. During an intervention, fluoroscopy images are obtained in act 36. The fluoroscopy images are obtained by transfer, scanning, or loading from memory. For example, the same x-ray system used to acquire the CINE acquisition is used to acquire frames of fluoroscopy data. X-rays are transmitted into and detected after passing through the patient. The fluoroscopy scanning is at a same angle as the CINE acquisition relative to the patient. The x-ray dose or intensity for the fluoroscopy scanning may be less than for the CINE acquisition, since the fluoroscopy scanning may occur over a longer period of time during the intervention, such as over tens or hundreds of heart cycles. Any fluoroscopy imaging may be used.

The frames of fluoroscopy data represent the same or similar region of the patient. Since the same vessel structure is in the images, the vessel structure may be represented. Since the guide wire is also still in the images, the guide wire may be represented. Due to the lack of added contrast agent and lower dose (i.e., lower x-ray intensity), the frames of data may not show the structures as well or with as much contrast as in the CINE acquisition.

The frames of fluoroscopy data are synchronized or time labeled with the ECG. For example, the phase for each frame is determined or labeled using ECG information. In other embodiments, the acquisition or scan for fluoroscopy is triggered based on the phase information from the ECG. The frames of fluoroscopy data are acquired at the same phases, frame rate, or both as the CINE acquisitions. Different phases and/or frame rate may be used.

In one embodiment, the patient is injected with dye after or while a guide wire, catheter or both are inserted into the patient. The CINE acquisition is performed with the guide wire positioned in the patient but not at or not being used to treat. For final placement of the guide wire and/or for treatment, fluoroscopy scanning is performed for monitoring the intervention. During the fluoroscopy, there may be less or no added or injected contrast agent (e.g., dye) in the patient. The fluoroscopy scanning is performed during later occurring heart cycles of the same patient as the CINE acquisition.

In act 38, the shape and/or location of the structure (e.g., guide wire, other medical device, and/or vessel) in the frames of fluoroscopy data is predicted. By finding locations of the structure, the shape is also provided. The location refers to any length of the structure, such as the entirety of the structure as represented in the scanned region or frame of fluoroscopy data. Only a portion of the structure in the scan region may be found in other embodiments.

The location is predicted using the periodic, time-varying model. For tracking the structure using the model, the phase information is used. The tracking is performed by estimating the location of the structure in each or a given frame of fluoroscopy data. By estimating the locations in different frames of the sequence, the structure is tracked. In other embodiments, the location from another phase informs or is used for finding the location in a current phase.

To track, the curve of the periodic time-varying model at the same phase as the frame of fluoroscopy data is used. The curve is registered to the fluoroscopy data for the frame to find a best fit. The frame of fluoroscopy data is used to distort (e.g., translate, rotate, and/or scale in rigid or affine adjustment) the model curve. In one embodiment, the curve from the model for each phase is used to locate the structure in frames of fluoroscopy data of the respective phase.

In another embodiment, the registration of a model curve with fluoroscopy data for different phase is used to refine the model curve for registering in a current phase. For example, the time-varying model is refined for the current phase based on the spatial translation of the time-varying model of the previous phase. Only rigid spatial translation along two axes is used. Non-rigid translation may be used. In other embodiments, rotation and/or scale may be used with or instead of spatial translation (e.g., shift of off-set along one or more of two axes).

The refining of the curve may account for systematic shifts constant or similar throughout the cycle. In an initiation, the registration of the curve from the model with a first frame of fluoroscopy data is performed without refining the model. Based on the registration, a translation, such as motion vector, placing the curve rigidly as close as possible to the detected structure or placing the curve in an affine manner, is determined. Using a best-fit in a least squares or other measure, the deformation in spatial translation is found.

For subsequent registrations, the curve of the model is refined by translation based on the previous registration. For example in tracking of the guide wire, the constructed time-varying curve model $y(\tau):[0,1]^R \to \Re^{DK}$ (where the phase $\tau$ is time-dependent) is used as a first estimate $\hat{y}(t_n)$ of the curve at time $t_n$. This estimate is refined by applying a spatial translation $\hat{T}(t_n)$ which is estimated from a previous time point $t_{n-k}$, $k=1, 2, \ldots$. The offset along one or two dimensions of the modeled curve of one phase from the image of that phase is used to offset the modeled curve of another phase for registering with the image of the other phase.

The translation determined for one or more other phases may be used to inform the translation for a current phase. For example, a mean translation from other registrations is used. In one embodiment, the spatial translation $\hat{T}(t_n)$ for refining a curve of the model is a weighted mean of any number of past translations between curve estimate $\hat{y}(t_n)$ and tracking result $y(t_n)$ from registration. For example $$\hat{T}(t_n) = \begin{cases} w \cdot T(\hat{y}(t_{n-1}), y(t_{n-1})) + (1-w) \cdot \hat{T}(t_{n-1}) & n > n_0 \\ T(\hat{y}(t_{n-1}), y(t_{n-1})) & n = n_0 \end{cases}$$

where the weight, w, determines the rate of decay of influence of past tracking results (e.g., w=0.7). Finite impulse response approaches may be used instead of infinite impulse response. In an alternative implementation, the estimated translation $\hat{T}(t_n)$ to refine the model curve may also be regressed from past time points in fluoroscopy. In this context, an online implementation of linear regression may be used. Other approaches for refining may be used.

After refining the curve of the model for a given phase or without refining, the curve of the model is registered with the fluoroscopy image. The frame of fluoroscopy data and curve of the model are selected to have a same or similar phase given the periodic nature of the motion and model. Similar may account for selecting a nearest phase, such as where the phases of the fluoroscopy image are between phases of the model. The registration estimates the shape and/or location of the structure (e.g., guide wire and/or vessel) in the fluoroscopy image.

Any registration may be used. For example, different translations, rotations, and/or scaling are performed to find a fit of the modeled curve with a minimum sum of absolute differences to the image. A cross-correlation may be used. Least squares fitting or other fitting may be used. The curve or refined curve of the model provides a starting point for the expected location, shape, and/or size of the structure. The registration finds a best fit localized to the expectation based on the periodic, time-varying model.

In one embodiment, a sequence of global and local deformation is applied to find the fit. The refined estimate $\hat{y}^*(t_n)$ is registered with image information, leading to the final tracking result $y(t_n)$ for that time-point. For registration, (1) global rigid deformation with spatial translation and rotation is performed. Then, (2) a global affine deformation is performed. The global affine deformation adjusts the scale for the entire curve. Lastly, (3) a local affine deformation is used to adjust different locations along the curve by different amounts to the frame of fluoroscopy data. Other hierarchal approaches may be used or a single or iterative approach for all of translation, rotation, and scale together may be used.

The registration indicates where the expected or modeled curve is located in the fluoroscopy data. Given known relationships of the modeled curve to other structure, the location of other structure may be found in the frame of fluoroscopy data. For example, the location of a treatment region (e.g., stenosis) is known relative to the modeled curve from the CINE acquisition. By finding the structure in the frame of fluoroscopy data, the location of the treatment region may be estimated. Alternatively, the treatment region is located as a structure using the modeling and registration.

In act 40, one or more fluoroscopy images are generated on a display. The fluoroscopy image shows the curved structure. Since the dose is low and no contrast agents are provided, the curved structure may be difficult for a viewer to locate quickly during an intervention. To provide more rapid reference for the view, the location of the structure is indicated in the image. The image is highlighted to show the structure. For example, color is added to show the structure (e.g., color the locations for the structure in blue or red on a gray scale fluoroscopy image). Another example is to provide a graphic overlay. A line of any color, such as a uniformly black or white curve, is overlaid as a graphic on the fluoroscopy image. For example, FIG. 2 shows a line as a graphic overlay in a fluoroscopy image.

The same or different indication may be used for different structures. For example, modeling is used to locate two structures, such as a guide wire and a vessel with a stenosis. Different graphic overlays or the same graphic overlay indicates both structures, highlighting the structures relative to the remainder of the gray scale image.

The indication is provided in each fluoroscopy image displayed to the user during the intervention. As additional images are displayed, the periodic, time-varying model is used to locate the structure in the image, and an indication of the location is provided. The sequence of fluoroscopy images over one or more (e.g., tens or hundreds) of heart cycles includes indications of the located structure or structure found in each of the images. For example, each image of the sequence includes a graphic overlay of the target vessel based on the tracking of the curved guide wire or other medical device. Phase information is used to determine the location for the indication through the various cycles. In alternative embodiments, the indication is provided on fewer than all of the displayed fluoroscopy images.

FIG. 1 shows a system 10 for modeling in angiography. Structure, such as a guide wire, is modeled. The modeling enforces periodicity using a multivariate curved regression. Curves are fitted to images with greater contrast or resolution by modeling, and then the fitted curves are used to locate the structure in images with less contrast or resolution.

The system 10 includes a memory 12, an angiography system 14, a guide wire 24, a processor 26, and a display 28. Additional, different, or fewer components may be provided. For example, a network or network connection is provided, such as for networking with a medical imaging network or data archival system. As another example, a preoperative imaging system, such as a computed tomography or magnetic resonance imaging system, is provided. In another example, a user interface is provided.

The processor 26 and display 28 are part of a medical imaging system, such as the angiography system 14. Alternatively, the processor 26 and display 28 are part of an archival and/or image processing system, such as associated with a medical records database workstation or server. In other embodiments, the processor 26 and display 28 are a personal computer, such as desktop or laptop, a workstation, a server, or combinations thereof. The processor 26, display 28, and memory 12 may be provided without other components for implementing the method.

The system 10, the processor 26, the angiography system 14, other components, or combinations thereof implement the acts of FIGS. 2 and/or 3. For example, the processor 26 performs all the acts. As another example, the processor 26 just performs acts 32, 34, and 38. The processor 26 may control other components or benefits from the performance of other components of acts 30, 36, and/or 40.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing frames of data or image information. The memory 12 is part of an imaging system, part of a computer associated with the processor 26, part of a database, part of another system, a picture archival memory, or a standalone device.

The memory 12 stores data representing a region, at different times, of a patient. The data includes information representing the guide wire 24 and/or other structure while in the region. The guide wire 24 may be difficult to recognize relative to other structures in the region in fluoroscopy images. The region is a two or three-dimensional region. The region is of any part of the patient, such as a region within the chest, abdomen, leg, head, arm, or combinations thereof.

The data is from scanning the region by x-rays, but other medical imaging modality may be used. In one embodiment, the data representing the patient is a projection of x-ray data, angiography data, fluoroscopy data, or combinations thereof. The data represents the patient prior to or during treatment. For example, angiography or fluoroscopy data is acquired during a catheterization or other intervention. As another example, contrast angiography or CINE acquisition data is acquired prior to intervention, such as just prior to (same day or as part of the intervention procedure) acquiring the fluoroscopy data.

As an alternative or in addition to storing image data, the memory 12 stores observed curves, fitted curves, the periodic time-varying model, phase measurements, synchronization information, graphic overlays, locations of structure, and/or other information.

The memory 12 or other memory is alternatively or additionally a computer readable storage medium storing data representing instructions executable by the programmed processor 26 for modeling in angiography. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The x-ray angiography system 14 is any now known or later developed angiography system. For example, the angiography system 14 includes an x-ray source and an x-ray detector on a C-arm or other robotic mechanism for positioning relative to the patient. The angiography system 14 includes position sensors for determining changes in position of the x-ray source and/or detector. In alternative embodiments, the angiography system 14 is a CT angiography or MR angiography system.

For angiography imaging, a contrast agent (e.g., iodine) may be injected into a patient. The contrast agent provides a detectable response to x-rays. By flowing through the circulatory system, the contrast agent may provide detectable response highlighting the circulatory system, such as the vessels, veins, and/or heart. Alternatively, no contrast agent is injected for fluoroscopic imaging. By transmitting x-rays through the patient to the detector, a projection image is provided. Any tissue, bone, catheter, guide wire 24, and contrast agent along the path of travel of the x-ray beam interacts with the x-rays, causing a detectable difference in intensity at the detector. Since each pixel or location of the detector represents an accumulation of responses along the path of travel, the fluoroscopic image is a projection image of the region.

An angiographic image may be generated with or without response from the guide wire 24. During intervention, the guide wire 24 may be positioned within the patient. One or more angiographic images are generated in real-time or during the interventional procedure. The x-ray beam of the angiography system 14 may pass through or intersect the patient volume. For example, the guide wire 24 is to be used for ablation of heart wall tissue, for ultrasound scanning to assist in stent placement, or for other imaging of the heart or circulatory system. The patient volume includes at least a portion of the heart. The x-ray beam is positioned to also project through the heart.

The guide wire 24 is any now known or later developed steering wire or treatment guide for intervention or other use within a patient. The guide wire 24 may be part of or operate with a catheter, so is sized and shaped for use in the circulatory system, such as having a diameter of 10 French or less, but a length of a foot or more. The guide wire 24 is adapted for insertion within the patient, such as through a vessel or vein for extending into a vessel or heart chamber. The guide wire 24 may be inserted through another previously positioned guide catheter. The guide wire 24 may include an electrode, scalpel, balloon, stent, or other device for treatment of the heart or circulatory system.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position, modeling, or tracking. The processor 26 is a single device or multiple devices operating in serial, parallel, or separately. The processor 26 may be a main processor of a computer, such as a laptop or desktop computer, or may be a processor for handling some tasks in a larger system, such as in an imaging system. The processor 26 is configured by instructions, design, hardware, and/or software to be able to perform the acts discussed herein, such as modeling and tracking using the modeling.

In one embodiment, the processor 26 is configured to estimate position, for each of different phases, of the guide wire 24 and/or other structure from image data. The processor 26 detects or receives detection results of locations of the structure (e.g., guide wire 24) from CINE acquisition information (e.g., x-ray images responsive to injected contrast agents) or other image data. The processor 26 fits curves to the observed structure. Using a regressor with sine, cosine, or sine and cosine features, the processor 26 fits the curves of the model with a repeating or periodic arrangement. The periodic, time-varying model of curves at different phases of a physiological cycle is constructed by the processor 26.

The processor 26 is configured to locate the guide wire 24 in fluoroscopy images. The constructed model includes different curves for different phases. Each fluoroscopy image is acquired at a phase. Different fluoroscopy images are acquired at different phases. A curve for the same phase or closest phase is matched to the fluoroscopy image. The curve is registered to the image. The image is used as feedback to locate the guide wire 24 or other structure with the modeled curve. The modeled curve assists in locating the structure since the fluoroscopy images have a lower vessel contrast, lower dose, more noise, and/or less distinct representation of the guide wire 24 or other structure than the CINE acquisition information or images acquired with a higher dose and/or added contrast agent. The modeled curve may be refined by translations, rotations, and/or scales of other registrations prior to being registered to the fluoroscopy data of a given image.

The processor 26 determines a structure position relative to the patient region or within an image. The position may be determined for assisting medical professionals by display of the image with the structure highlighted. For example, the processor 26 is configured to calculate a location of the guide wire 24 and/or vessel in the region as represented by the data. The location is a point, line, area, volume or surface location. For example, the location is a curve along a length of the guide wire as viewed in projection.

The display 28 is a monitor, LCD, projector, plasma display, CRT, printer, or other now known or later developed devise for outputting visual information. The display 28 receives images, graphics, or other information from the processor 26, memory 12, or angiography system 14.

One or more images representing a structure position relative to a patient region are displayed. The image may be of a location, such as displaying coordinates. The image may be of a medical scan representing the region of the patient. The location of the structure is highlighted, marked by a graphic, or otherwise indicated on the image. For example, an image includes fluoroscopic information showing the location of a guide wire 24 and vessel with a stenosis. Where a sequence of images is displayed, the location of each structure is indicated in each of the images. For example, fluoroscopy images for different phases are displayed with added highlighting or alteration to more strongly indicate the location of the guide wire 24 and/or other structure.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for modeling in angiography, the method comprising:
   obtaining a first sequence of frames of CINE acquisition data, the CINE acquisition data of the frames representing a curved medical device over a physiological cycle;
   identifying an observed curve for each of a plurality of different phases of the physiological cycle from the first sequence of CINE acquisition data;
   generating a fitted curve for each of the observed curves;

generating a motion model of the curved medical device as a function of the fitted curves;

obtaining a second sequence of frames of fluoroscopy data, the fluoroscopy data of the frames representing the curved medical device over the physiological cycle;

predicting the shape of the curved medical device in the frames of the fluoroscopy data as a function of the motion model of the curved medical device; and generating a fluoroscopy image of the curved medical device, the fluoroscopy image indicating the predicted curved medical device.

2. The method of claim 1 wherein obtaining the first sequence comprises obtaining the frames of CINE acquisition data responsive to injected contrast agents over multiple heart cycles, and wherein obtaining the second sequence comprises obtaining the frames of fluoroscopy data without injected contrast agents over multiple, later occurring heart cycles.

3. The method of claim 1 wherein generating a motion model comprises performing a multivariate curve regression.

4. The method of claim 3 wherein performing the multivariate curve regression comprises performing with smoothness constraints between points of a curve.

5. The method of claim 1 wherein generating a motion model comprises enforcing periodic behavior of the motion model with a feature vector of cosine, sine, or cosine and sine terms.

6. The method of claim 1 wherein predicting comprises registering the motion model for a first phase with a first frame of the fluoroscopy data for the first phase.

7. The method of claim 6 wherein registering comprises applying global and local deformations in sequence.

8. The method of claim 1 wherein predicting comprises refining the motion model for a first phase based on a spatial translation of the motion model for a second phase.

9. The method of claim 8 wherein refining comprises refining based on the spatial translation for the second phase and at least another spatial translation for another phase, a mean translation from the second phase and the other phase used to refining the motion for the first phase.

10. The method of claim 1 wherein generating comprises generating the fluoroscopy image as one in a sequence, each of the fluoroscopy images including a graphic overlay of a target vessel based on the tracking of the curved medical device.

11. The method of claim 1, wherein the plurality of different phases of the physiological cycle correspond to a plurality of breath phases.

12. In a non-transitory computer readable storage medium having stored therein data representing instructions executable by a programmed processor for modeling in angiography, the storage medium comprising instructions for:

generating a fitted curve for each of a plurality of observed curves of a curved medical device for each of a plurality of different phases of a physiological cycle from first images of a patient;

creating a periodic time-varying model of a curved medical device from the fitted curves;

predicting a shape of the curved medical device in second images of the patient with the periodic time-varying model, the predicting being a function of phase of a cycle; and displaying a sequence of the second images with the curved medical device enhanced using the predicted shape.

13. The non-transitory computer readable storage medium of claim 12 wherein creating comprises performing a multivariate curve regression on the curved medical device as detected from the first image.

14. The non-transitory computer readable storage medium of claim 13 wherein creating comprises enforcing periodic behavior of the periodic time-varying model in the regression with sine and cosine features.

15. The non-transitory computer readable storage medium of claim 12 wherein creating comprises estimating a regressor with minimization of an energy function including parameters of the regressor.

16. The non-transitory computer readable storage medium of claim 15 wherein creating comprises constraining the estimating between points of a curve of the curved medical device and constraining differences between features of the energy function.

17. The non-transitory computer readable storage medium of claim 12 wherein predicting comprises registering estimates of the shapes from the periodic time-varying model for different ones of the phases with the second images.

18. The non-transitory computer readable storage medium of claim 17 wherein registering comprises refining the estimates for each phase as a function of translations at other phases and then registering the refined estimates.

19. A system for modeling in angiography, the system comprising:

a memory operable to store data representing, at different times, a region of a patient and a curved medical device in the patient;

a processor configured to obtain a first sequence of frames of CINE acquisition data, the CINE acquisition data of the frames representing the curved medical device over a physiological cycle;

identify an observed curve for each of a plurality of different phases of the physiological cycle from the first sequence of CINE acquisition data;

generate a fitted curve for each of the observed curves;

generate a motion model of the curved medical device as a function of the fitted curves;

obtain a second sequence of frames of fluoroscopy data, the fluoroscopy data of the frames representing the curved medical device over the physiological cycle;

predict the shape of the curved medical device in the frames of the fluoroscopy data as a function of the motion model of the curved medical device; and a display operable to display a fluoroscopy image of the curved medical device, the fluoroscopy image indicating the predicted curved medical device.

20. The system of claim 19 wherein the processor generates a motion model by performing a multivariate curve regression.

* * * * *